United States Patent

Hotta et al.

[11] Patent Number: 4,478,753
[45] Date of Patent: Oct. 23, 1984

[54] PROCESS FOR THE PRODUCTION OF 11,11,12,12-TETRACYANO-9,10-ANTHRAQUINODIMEHANE OR ITS DERIVATIVES

[75] Inventors: Shu Hotta, Hirakata; Tomiharu Hosaka, Yawata; Nobuo Sonoda, Settsu; Wataru Shimotsuma, Ibaraki, all of Japan

[73] Assignee: Matsushita Electric Industrial Company, Limited, Japan

[21] Appl. No.: 426,069

[22] Filed: Sep. 28, 1982

[30] Foreign Application Priority Data

Sep. 29, 1981 [JP] Japan ................. 56-155592

[51] Int. Cl.$^3$ .......................... C07C 121/64
[52] U.S. Cl. .................. 260/396 N; 260/465 H
[58] Field of Search .............. 260/465 H, 396 N

[56] References Cited

U.S. PATENT DOCUMENTS 3,115,506 12/1963 Acker et al. ............... 260/396 N
3,687,987 8/1972 Martin .

OTHER PUBLICATIONS

Acker, D. C., et al. J. Am. Chem. Soc., 84, 3370 (1962).
Wheland, R. C., J. Org. Chem. vol. 40 (21), 3101 (1975).
Vincent, J. R., et al., J. Org. Chem., 3, 603 (1939).
The Journal of Organic Chemistry, vol. 31, No. 8, Aug. 1966 pp. 2618-2620; B. H. Klanderman: "Aldehyde Synthesis. A Study of the Preparation of 9,10-anthracenedicarboxaldehyde and other Aromatic Dialdehydes".

Primary Examiner—Dolph H. Torrence
Attorney, Agent, or Firm—Lowe, King, Price & Becker

[57] ABSTRACT

A process for producing 11,11,12,12-tetracyano-9,10-anthraquinodimethane or its derivatives of the general formula

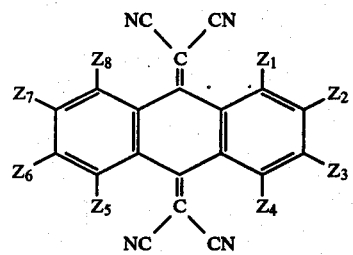

in which $Z_1$, $Z_4$, $Z_5$, and $Z_8$ independently represent hydrogen, chlorine, hydroxy or amino group and $Z_2$, $Z_3$, $Z_6$ and $Z_7$ independently represent hydrogen, halogen, alkyl which has 1 to 8 carbon atoms, phenyl, alkylphenyl whose alkyl group has 1 to 2 carbon atoms, hyroxyalkly which has 1 to 8 carbon atoms, carboxyalkyl whose alkyl group has 1 to 8 carbon atoms, hydroxy amino, or carboxyl group, the process comprising introduction of dicyanomethyl groups into an anthracene compound of the following general formula at 9 and 10 positions

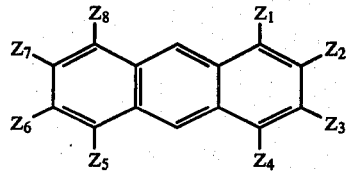

in which $Z_1$, $Z_2$, $Z_3$, $Z_4$, $Z_5$, $Z_6$, $Z_7$ and $Z_8$ have the same meanings as defined above, and dehydrogenation of the dicyanomethyl groups.

12 Claims, No Drawings

PROCESS FOR THE PRODUCTION OF 11,11,12,12-TETRACYANO-9,10-ANTHRAQUINODIMEHANE OR ITS DERIVATIVES

BACKGROUND OF THE INVENTION

Field of the Invention

This invention relates to a process for the production of 11,11,12,12-tetracyano-9,10-anthraquinodimethane or its derivatives (hereinafter referred to simply as TCNAQ or its derivatives).

Several organic semiconductive materials or compounds such as 7,7,8,8-tetracyanoquinodimethane or derivatives thereof (hereinafter referred to as TCNQ or its derivatives) have been produced and utilized in various fields because of their excellent semiconductive properties. Preparation of TCNQ derivatives is described, for example, by D. S. Acker et al., J. Am. Chem. Soc., 84, 3370 (1962), by R. C. Wheland, J. Org. Chem. 40 (21), 3101 (1975) and in U.S. Pat. No. 3,115,506. For instance, TCNQ is prepared by a method in which diethyl succinosuccinate used as a starting material is first converted into 1,4-cyclo-hexanedione and then reacted with malonitrile. The synthesis of 1,4-cyclohexanedione is particularly described by J. R. Vincent et al., J. Org. Chem., 3, 603 (1939) and the subsequent reaction is described in the report of Acker et al. mentioned above. As will be apparently noted from the literature of Vincent et al., the conversion of diethyl succinosuccinate into 1,4-cyclohexanedione involves hydrolysis and decarbonization reactions of diethyl succinosuccinate, which require very severe temperature conditions of 195° to 200° C. This imposes a great burden on the preparation of TCNQ.

On the other hand, Wheland et al. describe a method of preparing TCNQ derivatives. In this method, benzene derivatives, p-xylene derivatives or terephthalic acid derivatives are used as a starting material and converted into p-xylenehalides, followed by a sequence of reaction steps to obtain TCNQ derivatives. This method is disadvantageous in that a number of reaction steps are required for the preparation of the TCNQ derivatives and that tetracyano intermediate compounds obtained during the course of the reactions are sparingly soluble in ordinary solvents because of their high polarity. Accordingly, a large quantity of a solvent is required in the final reaction stage of obtaining TCNQ derivatives.

Thus, the known pfocesses of producing TCNQ or its derivatives disadvantageously involve extremely severe reaction conditions or a number of steps, say, seven or eight reaction steps. This is extremely disadvantageous in view of the reaction time, reaction yield and energy or power consumption required for the promotion of the reactions.

SUMMARY OF THE INVENTION

It is accordingly an object of the present invention to provide a process for producing TCNAQ or its derivatives having the tetracyanoquinodimethane skeletal structure under mild reaction conditions by a reduced number of reaction steps.

It is another object of the present invention to provide a process for producing TCNAQ or its derivatives which have wide utility in electrical and electronic fields similar to TCNQ compounds.

The above objects can be achieved by a process for producing a TCNAQ or derivatives thereof represented by the general formula (I)

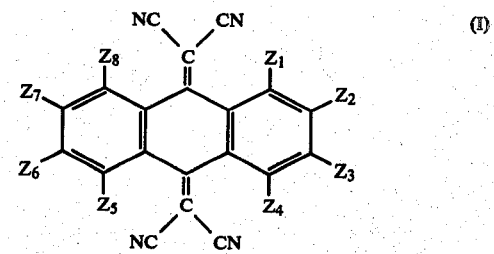

in which $Z_1$, $Z_4$, $Z_5$ and $Z_8$ independently represent hydrogen, chlorine, hydroxy or amino group and $Z_2$, $Z_3$, $Z_6$ and $Z_7$ independently represent hydrogen, halogen, alkyl having 1 to 8 carbon atoms, phenyl, alkylphenyl whose alkyl group has 1 to 2 carbon atoms, hydroxyalkyl whose alkyl group has 1 to 8 carbon atoms or carboxyalkyl whose alkyl group has 1 to 8 carbon atoms, hydroxy, amino or carboxyl group, which process comprising the steps of providing an anthracene compound of the general formula (II)

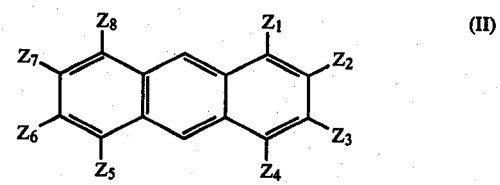

in which $Z_1$, $Z_2$, $Z_3$, $Z_4$, $Z_5$, $Z_6$, $Z_7$ and $Z_8$ have the same meanings as defined above, respectively, introducing dicyanomethyl groups into the anthracene compound at 9 and 10 positions, and subjecting the dicyanomethylated compound to the dehydrogenation reaction to obtain 11,11,12,12-tetracyano-9,10-anthraquinodimethane compound of the general formula (I). The dehydrogenation reaction is usually effected using a halogen such as chlorine, bromine or iodine as it is or in the form of an aqueous solution.

That is, the present invention is characterized by the reaction process which comprises (a) introduction of dicyanomethyl groups into anthracene compounds including anthracene itself at 9 and 10 positions thereof, and (b) conversion of the dicyanomethyl groups of the anthracene compound into dicyanomethylene groups by dehydrogenation.

In a more specific aspect, there is provided a process for producing a TCNAQ compound of the general formula (I) defined above, which process comprising the steps of, after halogenomethylation and formylation of an anthracene compound of the general formula (II), dihalogenomethylating the formylated anthracene compound with a halide compound in a solvent at a temperature ranging from 10° to 40° C., reacting the dihalogenomethylated product with a cyanide in a solvent at a temperature ranging from 100° to 180° C. and adding a halogen or an aqueous solution of a halogen selected from the group consisting of chlorine, bromine and iodine to the dicyanomethylated product obtained in the preceding step after dissolution of the product in a solvent miscible with water for dehydrogenation at a temperature ranging from −20° to 30° C. to obtain a dehydrogenated product represented by the general formula (I).

DETAILED DESCRIPTION OF THE INVENTION

Broadly, the production process according to the present invention can be represented by a sequence of the following reaction formulas (III)a and (III)b:

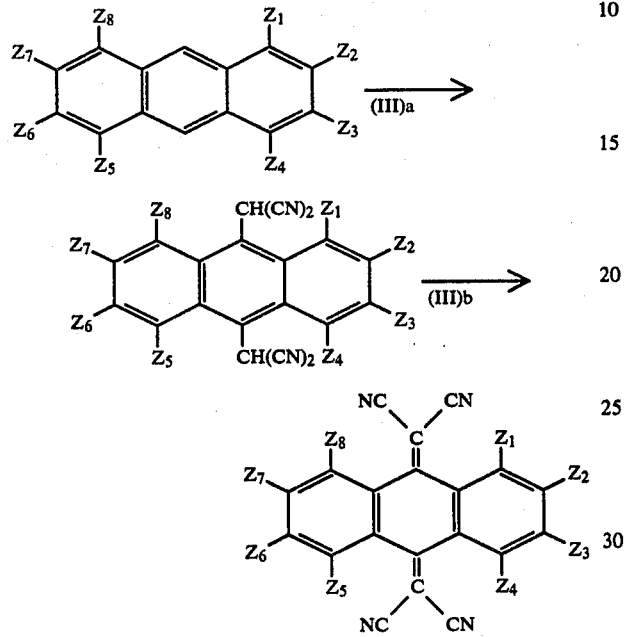

The first dicyanomethylation reaction may be effected by several procedures. A typical and preferable procedure is that which comprises halogenomethylating anthracene or its derivatives at 9 and 10 positions thereof, formylating and then dihalogenomethylating the resulting halogenomethylated anthracene or derivative thereof, and finally converting the dihalogenomethyl groups into dicyanomethyl groups. It should be noted that the halogen atom used for the halogenomethylation and dihalogenomethylation should be chlorine, bromine or iodine. Alternatively, an anthracene compound may be introduced with dicyanomethyl groups at 9 and 10 positions by dissolving the compound in a solvent such as benzene, suspending a Lewis acid used for the Friedel-Krafts reaction therein, and dissolving a monohalogenated malonitrile in the solution and agtating it at room temperature for several hours. The Lewis acids used above are, for example, aluminium halides, ferric chloride, tin chloride, titanium chloride and zinc chloride. In the case, the Lewis acid is added in an amount exceeding an equivalent amount of the monohydrogenated malonitrile. Although the formylated anthracene compounds may be prepared by either of the methods, the former procedure is preferable to the latter procedure because of higher yields and more rapid reaction velocity.

On the other hand, the procedure (III)b can be caused to smoothly proceed using a halogen and water or a halogen alone.

The reaction procedures prior to the dihalogenomethylation of the preferable procedure, i.e. the halogenomethylation and formylation, are described, for example, by B. H. Klendelman, J. Org. Chem., 31, 2618 (1966). This reference is incorporated herein by reference. Accordingly, the reaction steps including the formylation and preceding reactions are described only briefly. That is, an anthracene compound is halogenomethylated with a halogenomethylating agent such as a mixture of paraformaldehyde and hydrogen chloride under conditions of a temperature of 40° to 90° C. and 0.5 to 5 hours. Then, the resulting product is formylated with 2-nitropropane under conditions of 10° to 40° C. and 0.5 to 5 hours. By this, a formylated product is obtained.

The reaction steps subsequent to the formylation are summarized in the following sequence of reactions of the formulas (IV)a through (IV)c in which formylated anthracene is used as a starting material:

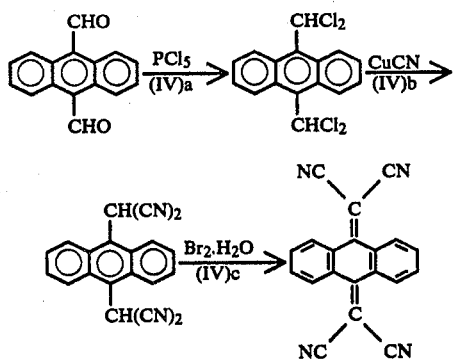

In general, the sequence of the reactions indicated above proceed under slightly heating conditions or at room or lower temperatures. Accordingly, an energy or power consumption required for effecting the reactions is much smaller than those for the known processes. Moreover, these reactions are all simple substitution and elimination reactions with side reactions hardly occuring and thus TCNAQ or its derivatives can be obtained in high yields ranging from 10 to 80 mole % based on the starting anthracene or derivatives thereof.

The reaction of the formula (IV)a is dihalogenomethylation of a formylated product, in which the formylated product is reacted with halide compounds including phosphorus halides such as phosphorus pentachloride, phosphorus pentabromide, phosphorus pentaiodide, $POCl_3$, $POBr_3$, $POI_3$ and the like and $AOX_2$ in which A represents C or S and X represents Cl, Br, I or a mixture thereof in a solvent at a temperature ranging from 10° to 40° C. for 0.5 to 5 hours. The solvents useful for the above purpose are polar solvents such as dichloromethane, chloroform, trichloroethylene and the like. The reaction is preferably conducted under agitation conditions at temperature of 20° to 30° C. for 1 to 4 hours. The resulting product is preferably recrystallized from a solvent of the type used above and employed for the subsequent dicyanomethylation reaction.

The dihalogenomethylated product is then reacted with a cyanide such as cuprous cyanide, sodium cyanide, potassium cyanide or the like in a solvent at a temperature ranging from 100° to 180° C., preferably 120° to 160° C., for 0.5 to 10, preferably 2 to 5, hours under agitation. More preferably, the reaction is effected under reflux. Examples of the solvent suitable for the purpose include mixed solvents such as a combination of dimethylformamide and water in various mixing ratios, a combination of dimethylsulfoxide and water and the like. After completion of the reaction, the dicyanomethylated product which separates as crystals is collected such as by filtration. The thus collected product is then subjected to the dehydrogenation reaction with or without purification such as by recrystallization as usual.

The dicyanomethylated product is then dissolved in a solvent miscible with water, to which is added a halogen or an aqueous halogen solution in excess of the theoretical amount required for the dehydrogenation of the dicyanomethylated compound. The mixture is agitated at a temperature ranging from 10° to 30°, preferably at 20° to 30° C., for 0.5 to 2 hours for dehydrogenation in the presence of an organic base such as pyridine, picoline or the like. Then, the mixture is allowed to stand for a time sufficient for crystallization, e.g. at least 4 hours while cooling to a temperature of −20° to 10° C. As a result, a dehydrogenated product is obtained as crystals. The crystals are collected by suitable means and recrystallized from a suitable solvent such as o-dichlorobenzene, dichloromethane, benzonitrile, acetonitrile or the like.

The solvents miscible with water are, for example, acetonitrile, dimethylformamide, tetrahydrofuran, 1,3-dioxane and the like.

In general, the aqueous halogen solution has a halogen concentration of 0.5 to 10 wt % of the solution. The halogen other than fluorine is used for this purpose.

The starting anthracene materials useful in the practice of are those represented by the general formula (I) and specific and preferable examples of the anthracene materials include anthracene, 2-fluoroanthracene, 2-chloroanthracene, 2-bromoanthracene, 7-chloro-2-ethylanthracene, 1-chloroanthracene, 1,4-dichloroanthracene, 2,3-dichloroanthracene, 2,3-dibromoanthracene, anthracene-2-carboxylic acid, 1-aminoanthracene, 2-aminoanthracene, 1-hydroxyanthracene, 2-hydroxyanthracene, 2,3-dihydroxyanthracene, 1,5-dihydroxyanthracene, 2-methylanthracene, 2-ethylanthracene, 2-(2-hydroxyethyl)anthracene, 2-(3-carboxypropyl)anthracene, 2-phenylanthracene, 2(2-methylphenyl) anthracene, 2-(4-ethylphenyl)anthracene and the like. These anthracene compounds may be commercially available or may be readily prepared by any known techniques. Of these anthracene compounds, anthracene is most preferably used because it can be obtained in large quantities and inexpensively from coal tar.

In case where amino derivatives of anthracene are used as a starting material, it is necessary that the amino group is protected by converting into acetylamino group by means of acetyl chloride or the like prior to commencement of the sequence of the reactions and then the acetylated amino derivatives are subjected to the reactions according to the present invention. After formation of a TCNAQ derivative, the acetylamino protective group is finally converted into the original amino group with use of a reducing agent such as hydrazine or the like. The protection of the amino group similar to the above procedure is described, for example, in Bull. Chem. Soc. Japan, 39, 185 (1966) by M. Fujinaga et al.

On the other hand, when hydroxy derivatives of anthracene are used as a starting material, the hydroxy group or groups are protected by converting, prior to the sequence of the reactions of the invention, into methoxy or similar groups by the use of a suitable agent such as methyl iodide and silver oxide, followed by the procedure of the invention. After formation of a TCNAQ derivative, the methoxy group or groups are reconverted into the hydroxy groups with use of, for example, concentrated sulfuric acid. The protection of hydroxy groups is described, for example, by J. C. Lovie et al., J. Chem. Soc., 4139 (1959). On the other hand, the conversion of methoxy groups into hydroxy groups is described, for example, by T. A. Geisman et al., J. Am. Chem. Soc., 73, 5765 (1951).

The present invention is particularly described by way of examples which should not be construed as limiting the present invention.

EXAMPLE 1

According to the method of Klendelman et al. mentioned before, 9,10-diformylanthracene was obtained from anthracene by the following procedure. A mixture of 180 ml of 1,4-dioxane, 30 ml of 35% concentrated hydrochloric acid and 22.5 g of paraformaldehyde was agitated, into which was charged 21 g of anthracene, followed by further agitating while blowing hydrogen chloride gas thereinto. The reaction was effected at a temperature of 80° to 85° C. for 2 hours. Thereafter, the reaction solution was allowed to stand over day and night and filtered. The resulting cake was recrystallized from 1,4-dioxane to obtain 17 g of 9,10-bis(chloromethyl)-anthracene in the form of crystals.

5 g of the crystals were weighed and charged into a mixed solution of 100 ml of dimethylsulfoxide, 40 ml of ethanol and 10 g of 2-nitropropane, followed by agitating at room temperature for 3 hours and charging into iced water thereby obtaining crystals. The crystals were separated by filtration and recrystallized from dichloromethane to obtain 9,10-diformylanthracene. Then, 3 g of 9,10-diformylanthracene and 5 g of phosphorus pentachloride were dissolved in 50 ml of dichloromethane, followed by agitation at room temperature for 4 hours. The resulting product was recrystallized from dichloromethane to obtain 2.6 g of 9,10-bis(dichloromethyl) anthracene was obtained as crystals.

The crystals were dissolved together with 9 g of cuprous cyanide in a mixed solvent of dimethylformamide and water in a mixing ratio of 1:1, followed by agitating at 100° C. for 4 hours. The resulting product was collected and recrystallized from acetonitrile to obtain 1.1 g of 9,10-bis(dicyanomethyl)-anthracene in the form of crystals.

All the crystals were then dissolvd in 50 ml of acetonitrile. To the solution was added an excess of bromine and 5 ml of pyridine as a catalyst. The mixture was agitated at room temperature for 30 minutes, followed by allowing to stand over day and night while cooling the reaction system with iced water to obtain a precipitate as crystals. The crystals were recrystallized from o-dichlorobenzene to obtain 0.7 g of TCNAQ as crystals.

The thus obtained crystals were subjected to the mass spectrometry, revealing that the compound had a composition of $C_{20}H_8N_4$ with very small amounts of other elements. Moreover, the infrared absorption spectroscopy demonstrated characteristic absorption peaks indicated in Table 1 below, in which the wave numbers of the absorption peaks and functional groups to which the respective peaks are attributed are shown.

TABLE 1

| Characteristic Absorption Spectra of Functional Groups | |
|---|---|
| Vibration Mode of Functional Group | Wave Number (cm$^{-1}$) |
| C≡N stretching vibration of α,β-unsaturated nitrile | 2220 |

TABLE 1-continued

Characteristic Absorption Spectra of Functional Groups

| Vibration Mode of Functional Group | Wave Number (cm$^{-1}$) |
|---|---|
| C=C stretching vibration of α,β-unsaturated nitrile | 1540 |
| C—C stretching vibration of aromatic nucleus | 1450 |

EXAMPLE 2

Various anthracene derivatives were used to prepare corresponding TCNAQ derivatives in the same manner as in Example 1. In Table 2, there are shown anthracene derivatives and TCNAQ derivatives obtained from the anthracene derivatives. The infrared absorption spectroscopy of the TCNAQ derivatives revealed that characteristic absorption spectra similar to those of Example 1 were found near the wave numbers indicated in Table 1.

TABLE 2

| Anthracene Derivatives | TCNAQ Derivatives |
|---|---|
| 2-fluoroanthracene | 2-fluoro-TCNAQ |
| 2-chloroanthracene | 2-chloro-TCNAQ |
| 2-bromoanthracene | 2-bromo-TCNAQ |
| 7-chloro-2-ethylanthracene | 7-chloro-2-ethyl-TCNAQ |
| 1-chloroanthracene | 1-chloro-TCNAQ |
| 1,4-dichloroanthracene | 1,4-dichloro-TCNAQ |
| 2,3-dichloroanthracene | 2,3-dichloro-TCNAQ |
| 2,3-dibromoanthracene | 2,3-dibromo-TCNAQ |
| anthracene-2-carboxylic acid | 2-carboxy-TCNAQ |
| 1-aminoanthracene | 1-amino-TCNQ |
| 2-aminoanthracene | 2-amino-TCNAQ |
| 1-hydroxyanthracene | 1-hydroxy-TCNAQ |
| 2-hydroxyanthracene | 2-hydroxy-TCNAQ |
| 2,3-dihydroxyanthracene | 2,3-dihydroxy-TCNAQ |
| 1,5-dihydroxyanthracene | 1,5-dihydroxy-TCNAQ |
| 2-methylanthracene | 2-methyl-TCNAQ |
| 2-ethylanthracene | 2-ethyl-TCNAQ |
| 2-(2-hydroxyethyl)anthracene | 2-(2-hydroxyethyl)-TCNAQ |
| 2-(3-carboxypropyl)anthracene | 2-(3-carboxypropyl)-TCNAQ |
| 2-phenylanthracene | 2-phenyl-TCNAQ |
| 2-(2-methylphenyl)anthracene | 2-(2-methylphenyl)TCNAQ |
| 2-(4-ethylphenyl)anthracene | 2-(4-ethylphenyl)-TCNAQ |

Note:
In the Table, 2-chloro-11,11,12,12-tetracyano-9,10-anthraquinodimethane is abbreviated as 2-chloro-TCNAQ and this is true of other anthraquinodimethanes.

What is claimed is:

1. A process for producing a 11,11,12,12-tetracyano-9,10anthraquinodimethane of the general formula (I)

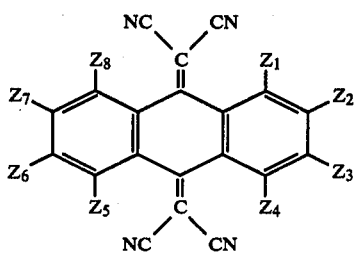

in which $Z_1$, $Z_4$, $Z_5$ and $Z_8$ independently represent hydrogen, chlorine, hydroxy or amino group, and $Z_2$, $Z_3$, $Z_6$ and $Z_7$ independently represent hydrogen, halogen, alkyl having 1 to 8 carbon atoms, phenyl, alkylphenyl whose alkyl group has 1 to 2 carbon atoms, hydroxyalkyl whose alkyl group has 1 to 8 carbon atoms, carboxyalkyl whose alkyl group has 1 to 8 carbon atoms, hydroxy, amino or carboxyl group, the process comprising the steps of:

(a) providing an anthracene compound of the general formula (II)

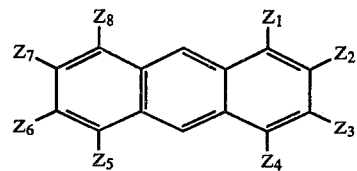

in which $Z_1$, $Z_2$, $Z_3$, $Z_4$, $Z_5$, $Z_6$, $Z_7$ and $Z_8$ have the same meanings as defined above, respectively:

(b) halomethylating the anthracene compound to introduce dicyanomethyl groups into the anthracene compound at the 9 and 10 positions;

(c) formylating the halogenomethylated compound at the halogenomethyl groups;

(d) dihalogenomethylating the formylated compound;

(e) dicyanomethylating the dihalogenomethylated compound; and (f) subjecting the dicyanomethylated compound to dehydrogenation to obtain the compound of the general formula (I).

2. A process according to claim 1, wherein the said dicyanomethylated compound is dehydrogenated by reaction with a halogen selected from the group consisting of chlorine, bromine and iodine in the presence of an organic base.

3. A process according to claim 1, wherein said anthracene compound is anthracene.

4. A process for producing a 11,11,12,12-tetracyano-9,10-anthraquinodimethane compound of the general formula (I)

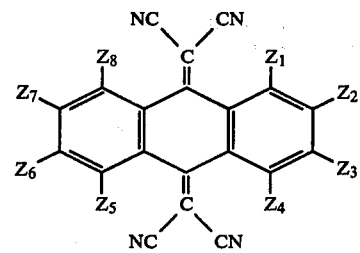

in which $Z_1$, $Z_4$, $Z_5$ and $Z_8$ independently represent hydrogen, chlorine, hydroxy or amino group, and $Z_2$, $Z_3$, $Z_6$ and $Z_7$ independently represent hydrogen, halogen, alkyl having 1 to 2 carbon atoms, phenyl, alkylphenyl whose alkyl group has 1 to 8 carbon atoms, hydroxyalkyl whose alkyl group has 1 to 8 carbon atoms, carboxyalkyl whose alkyl group has 1 to 8 carbon atoms, hydroxy, amino or carboxyl group, which process comprising the steps of:

(a) providing a formylated anthracene compound of the general formula (II)

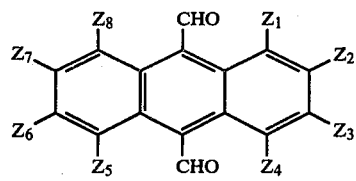

in which $Z_1$, $Z_2$, $Z_3$, $Z_4$, $Z_5$, $Z_6$, $Z_7$ and $Z_8$ have the same meanings as defined above, respectively;

(b) dihalogenomethylating the formylated anthracene compound by reaction with a phosphorus halide in a solvent at a temperature ranging from 10° to 40° C.;

(c) reacting the dihalogenomethylated product with a cyanide at a temperature ranging from 100° to 180° C.; and (d) adding a halogen selected from the group consisting of chlorine, bromine and iodine to the dicyanomethylated product obtained in the step (c), dissolving the dicyanomethylated product in a solvent miscible with water, and dehydrogenating at a temperature ranging from −20° to 30° C. thereby obtaining a dehydrogenated product of the general formula (I).

5. A process according to claim 4, wherein the dihalogenomethylation step (b) is effected at a temperature ranging from 20° to 30° C. for 1 to 4 hours in the presence of an organic base.

6. A process according to claim 4, wherein the dihalogenomethylated product obtained from step (b) is reacted with cuprous cyanide in step (c).

7. A process according to claim 6, wherein the reaction with cuprous cyanide is effected at a temperature ranging from 120° to 160° C. under agitation.

8. A process according to claim 7, wherein the reaction with cuprous cyanide is effected under reflux.

9. A process according to claim 4, wherein the halogen used for the dehydrogenation in step (d) is used in excess of the theoretical amount required for the dehydrogenation of the dicyanomethylated compound.

10. A process according to claim 4, wherein the halogen used in step (d) is contained in an aqueous solution and said aqueous solution has a concentration of 0.5 to 10 wt % of the halogen.

11. A process according to claim 4, wherein step (d), after the addition of a halogen, the solution is allowed to cool to a temperature of −20° to 10° C.

12. A process according to claim 4, wherein the anthracene compound of the general formula (II) is anthracene.

* * * * *

UNITED STATES PATENT AND TRADEMARK OFFICE
CERTIFICATE OF CORRECTION

PATENT NO. : 4,478,753
DATED : October 23, 1984
INVENTOR(S) : Shu HOTTA et al

It is certified that error appears in the above-identified patent and that said Letters Patent is hereby corrected as shown below:   Title page:

At [54], the title should read as follows:

-- PROCESS FOR THE PRODUCTION OF 11,11,12,12-TETRACYANO-9,10-ANTHRAQUINODIMETHANE OR ITS DERIVATIVES --

Signed and Sealed this

Sixteenth Day of April 1985

[SEAL]

Attest:

DONALD J. QUIGG

Attesting Officer

Acting Commissioner of Patents and Trademarks